United States Patent
Zhang et al.

(10) Patent No.: US 12,274,544 B2
(45) Date of Patent: Apr. 15, 2025

(54) SYSTEM FOR PRECISELY LOCATING ABNORMAL AREA OF BRAIN FIBER BUNDLE

(71) Applicant: ZHEJIANG LAB, Hangzhou (CN)

(72) Inventors: Yu Zhang, Hangzhou (CN); Chaoliang Sun, Hangzhou (CN); Zhichao Wang, Hangzhou (CN); Huan Zhang, Hangzhou (CN); Haotian Qian, Hangzhou (CN); Tianzi Jiang, Hangzhou (CN)

(73) Assignee: ZHEJIANG LAB, Hangzhou (CN)

( * ) Notice: Subject to any disclaimer, the term of this patent is extended or adjusted under 35 U.S.C. 154(b) by 0 days.

(21) Appl. No.: 18/796,264

(22) Filed: Aug. 6, 2024

(65) Prior Publication Data

US 2024/0389880 A1    Nov. 28, 2024

Related U.S. Application Data

(63) Continuation of application No. PCT/CN2023/124640, filed on Oct. 16, 2023.

(30) Foreign Application Priority Data

Oct. 19, 2022  (CN) .......................... 202211276171.8

(51) Int. Cl.
  *A61B 5/055*  (2006.01)
  *A61B 5/00*  (2006.01)
  *G06T 7/00*  (2017.01)

(52) U.S. Cl.
  CPC ............ *A61B 5/055* (2013.01); *A61B 5/0042* (2013.01); *A61B 5/7267* (2013.01);
  (Continued)

(58) Field of Classification Search
  CPC ..... A61B 5/055; A61B 5/0042; A61B 5/7267; G06T 7/0012; G06T 2207/10088; G06T 2207/30016
  See application file for complete search history.

(56) References Cited

U.S. PATENT DOCUMENTS 10,881,321 B2 *  1/2021  Verma .................... A61B 5/055
2008/0109171 A1   5/2008  McGraw et al.
(Continued)

FOREIGN PATENT DOCUMENTS

CN    103049901 A    4/2013
CN    104899884 A    9/2015
(Continued)

OTHER PUBLICATIONS

Wen 2019 PhD Computer Sciences Universite de la Sorbonne 236 pages (Year: 2019).*

(Continued)

*Primary Examiner* — Keith M Raymond
*Assistant Examiner* — Patrick M Mehl
(74) *Attorney, Agent, or Firm* — Wiersch Law Group

(57) ABSTRACT

A system for precisely locating abnormal areas of brain fiber bundles. The system extracts fiber connections of the whole brain from diffusion magnetic resonance data, and fiber bundle pathways extracts through self-defined fiber bundle pathways or based on brain fiber bundle templates. A selected fiber bundle pathway is projected on a fiber connection result of the whole brain and finely segmented. The imaging indexes such as fractional anisotropy, mean diffusivity, intra-neurite volume fraction and orientation dispersion index are calculated from diffusion magnetic resonance data, so as to obtain the imaging index of each node of each fiber bundle pathway. These imaging indexes are configured to classify the disease group and the healthy group by a
(Continued)

machine learning method, and which nodes on which fiber bundle pathways have abnormal changes with different diseases can be precisely located.

5 Claims, 2 Drawing Sheets

(52) U.S. Cl.
CPC .. *G06T 7/0012* (2013.01); *G06T 2207/10088* (2013.01); *G06T 2207/30016* (2013.01)

(56) References Cited

U.S. PATENT DOCUMENTS

| | | | |
|---|---|---|---|
| 2008/0205733 | A1 | 8/2008 | Laidlaw et al. |
| 2017/0052241 | A1* | 2/2017 | Cetingul .......... G01R 33/56341 |
| 2017/0220900 | A1* | 8/2017 | Boada .................... A61B 5/055 |
| 2017/0285124 | A1* | 10/2017 | Verma ................ G01R 33/5608 |
| 2018/0122074 | A1* | 5/2018 | Li ........................ A61B 5/7425 |
| 2022/0011392 | A1* | 1/2022 | Schwab ............... G06V 10/764 |
| 2022/0165004 | A1 | 5/2022 | Schwab et al. |

FOREIGN PATENT DOCUMENTS

| | | |
|---|---|---|
| CN | 106667490 A | 5/2017 |
| CN | 108734163 A | 11/2018 |
| CN | 110811622 A | 2/2020 |
| CN | 110827282 A | 2/2020 |
| CN | 110942489 A | 3/2020 |
| CN | 110992439 A | 4/2020 |
| CN | 113221952 A | 8/2021 |
| CN | 114120024 A | 3/2022 |
| CN | 114187258 A | 3/2022 |
| CN | 114494132 A | 5/2022 |
| CN | 114627283 A | 6/2022 |
| CN | 114842969 A | 8/2022 |
| CN | 114983389 A | 9/2022 |
| CN | 115170540 A | 10/2022 |
| CN | 115359305 A | 11/2022 |
| EP | 3407295 A1 | 11/2018 |
| TW | 201543380 A | 11/2015 |
| WO | 2011011554 A1 | 1/2011 |

OTHER PUBLICATIONS

Oladosu et al. 2021 Frontiers in Neuroscience 15:634063 13 pages (Year: 2021).*
Azer 2022 PhD Thesis Health Informatics Middle East Technical University Turkey 143 pages (Year: 2022).*
International Search Report (PCT/CN2023/124640); Date of Mailing: Jan. 20, 2024.
Notice of Allowance(202010087761.0); Date of Mailing: Dec. 5, 2022.
A-Fiber-Tracking-Algorithm-Based-on-Non-Local-Constrained-Spherical-Deconvolution.
A-new-proposal-for-3D-fiber-tracking-in-synthetic-diffusion-tensor-magnetic-resonance-images.
Application-of-diffusion-tensor-imaging-technique-in-white-matter-disease.
Notice Of Allowance(202211276171.8 ); Date of Mailing: Dec. 5, 2022.

* cited by examiner

SYSTEM FOR PRECISELY LOCATING ABNORMAL AREA OF BRAIN FIBER BUNDLE

CROSS-REFERENCE TO RELATED APPLICATIONS

The present application is a continuation of International Application No. PCT/CN2023/124640, filed on Oct. 16, 2023, which claims priority to Chinese Application No. 202211276171.8, filed on Oct. 19, 2022, the contents of both of which are incorporated herein by reference in their entireties.

TECHNICAL FIELD

The present disclosure relates to the field of neuroimage data analysis, and in particular, to a system for precisely locating abnormal areas of brain fiber bundles.

BACKGROUND

Diffusion-weighted magnetic resonance is a quantitative magnetic resonance imaging method. In traditional magnetic resonance, hydrogen protons in the human body are excited by applying a radio frequency pulse with a certain frequency to the human body in a magnetic field, resulting in resonance. After the pulse stops, the proton generates a magnetic resonance signal during the relaxation process. After encoding, receiving and reconstructing the magnetic resonance signal, a static structural image is generated. Diffusion-weighted magnetic resonance measures the diffusion movement of water molecules in human body, that is, the displacement of water within a predetermined diffusion time.

In homogeneous water, the diffusion movement of water molecules is a three-dimensional random movement, and the diffusion degree is the same in all directions. This phenomenon is called diffusion isotropy. In human body, the diffusion movement of water molecules in three-dimensional space is restricted by various restrictions. If the diffusion movement of water molecules is hindered by cell membranes and macromolecules, the displacement of water molecules will be reduced and the diffusion of water molecules will be hindered. For example, in the myelinated nerve fiber bundle, the diffusion movement of water molecules along the fiber orientation is much greater than that in the myelinated direction, which is called diffusion anisotropy.

Based on this principle, a diffusion tensor imaging (DTI) model is the development and improvement of magnetic resonance diffusion weighted imaging technology. The diffusion tensor model is a three-dimensional model, which quantifies the anisotropy signal of water molecule diffusion, and uses diffusion sensitive gradient pulse to expand the diffusion effect of water molecule to study the difference of water molecule diffusion movement in different tissues, so that the microstructure of brain tissue can be displayed more precisely. A neurite orientation dispersion and density imaging (NODDI) model divides microenvironment into three situations: intracellular, extracellular and cerebrospinal fluid. Each microenvironment affects the diffusion of water molecules in different ways, which can be used to evaluate the complexity of axon and dendrite microstructure and reflect the information of different tissues in brain tissue.

Diffusion magnetic resonance imaging can detect the microstructure features of the brain and the orientations of fiber bundles by measuring the diffusion difference of water molecules. Some commonly used parameters can be obtained by using these diffusion features. For example, indexes such as Fractional anisotropy (FA) and Mean diffusivity (MD) can be calculated by diffusion tensor imaging, and intra-neutrite volume fraction (ICVF) and orientation dispersion index (ODI) can further be calculated by neurite orientation dispersion index and density imaging. Moreover, the corresponding fiber bundle pathway can be extracted through the fiber tracking results at the whole brain level. Among them, FA reflects the ratio of the anisotropic part of diffusion to the total value of the diffusion tensor, which can be used to show the direction of nerve conduction bundles in white matter, observe the integrity and connectivity of the tissue structure, and assist in judging the degree and scope of white matter fiber bundle damage caused by various diseases. MD reflects the diffusion range of water molecules per unit time, such as the increase of water molecules with limited diffusion, which will cause the decrease of MD in this region. ICVF can reflect the nerve density, such as the density of axons. ODI can quantify the dispersion of neurite orientation, such as fan-shaped fibers and decussating fibers. These imaging indicators provide a variety of perspectives for the study of various diseases.

Fiber tracking is an important method for fiber bundle pathway analysis. The traditional fiber tracking method based on diffusion tensor imaging constructs the whole brain fiber bundles according to the tensor principal orientation, a preset deflection angle threshold, FA threshold and other parameters, and then tracks the specific fiber bundles by setting ROI, and calculates the number of fiber bundles, average FA and other related indicators, but it cannot solve the problem of decussating fibers.

A support vector machines (SVM) is a commonly used machine learning classification model. The basic idea of SVM learning is to solve a separation hyperplane which can correctly divide the training data set and has the largest geometric interval. The feature weights obtained by SVM can reflect which nodes of which fiber bundles are significantly different between the disease group and the healthy group.

In the past, the analysis methods of fiber bundle imaging were limited to the integral analysis of the whole brain or the fiber pathway, and only the differences between groups were simply compared statistically.

SUMMARY

In view of the shortcomings of the prior art, the present disclosure provides a system for precisely locating abnormal areas of brain fiber bundles. By estimating the response function of the diffusion magnetic resonance data and reconstructing a fiber orientation distribution diffusion model through constrained spherical deconvolution, the spherical deconvolution model can estimate the dispersion distribution of each voxel. Then, by using the probabilistic fiber tracing method, seed points are randomly set in the region of interest, and fiber bundles are tracked from each seed point until a specified number of fiber bundles are completed. Then, fiber bundles are screened by using a spherical deconvolution filter of fiber bundles, and fibers with physiological significance are retained, so that the number of local fibers tracked is proportional to the real local nerve fiber density. By defining initiate regions of interest, ending regions of interest, passed regions of interest and avoided regions of interest, fiber tracking is carried out based on seed points, and the fiber bundle pathway satisfying the region of interest can be obtained. Through the automatic quantitative method, the extracted fiber bundle of interest can be further segmented (such as 100 equal parts), and the imaging indexes on each small segment can be counted, so that the fiber bundle pathway can be analyzed more precisely. Finally, the SVM method is configured to classify the disease group and the healthy group and locate the abnormal nodes of the fiber bundle. According to the present disclosure, the fiber bundle pathways of interest can be obtained and finely segmented, and the imaging indexes of each diffusion model are effectively utilized. Through the method of machine learning, abnormal fiber bundles can be precisely located, and the focus of white matter-related diseases can be precisely located.

The present disclosure is realized by the following technical solution: a system for precisely locating abnormal areas of brain fiber bundles, including the following modules: a diffusion magnetic resonance data acquisition module, a diffusion magnetic resonance data preprocessing module, a whole brain fiber tracking module, a fiber bundle pathway of interest defining module, a fiber bundle pathway projection and segmentation module, a fiber bundle node image index extraction module, and a machine learning classification and abnormal node locating module.

The diffusion magnetic resonance data acquisition module is configured for acquiring diffusion magnetic resonance data from a disease group and a healthy group.

The diffusion magnetic resonance data preprocessing module is configured for denoising and correcting the diffusion magnetic resonance data acquired by the diffusion magnetic resonance data acquisition module.

The whole brain fiber tracking module is configured for extracting fiber connections of a whole brain based on the preprocessed diffusion magnetic resonance data.

The fiber bundle pathway of interest defining module is configured for self-defining a fiber bundle pathway or extracting a fiber bundle pathway based on a brain fiber bundle template.

The fiber bundle pathway projection and segmentation module is configured for projecting the fiber bundle pathway onto a fiber connection result of the whole brain and segmenting, and defining each segment as a node.

The fiber bundle node image index extraction module configured for calculating the anisotropy fraction, mean diffusivity, intra-neurite volume fraction and orientation dispersion index of the diffusion magnetic resonance data, so as to obtain the imaging indexes of each node of each fiber bundle pathway.

The machine learning classification and abnormal node locating module is configured for classifying the disease group and the healthy group by using imaging indexes through a machine learning method with taking features of each nerve fiber node as an input of a classifier and a group label of the subject as an output of the classifier, and locating which nodes on which fiber bundle pathways have abnormal changes with different diseases.

Further, the diffusion magnetic resonance data preprocessing module is configured for denoising the diffusion magnetic resonance data based on a principal component analysis (PCA) method, correcting a distortion based on out-of-phase coded images, and correcting head movement and eddy current on the diffusion magnetic resonance data.

Further, the whole brain fiber tracking module is configured for estimating a response function of the preprocessed diffusion magnetic resonance data, reconstructing a fiber orientation distribution diffusion model through constrained spherical deconvolution, and tracking whole brain fibers based on the reconstructed fiber orientation distribution diffusion model; and screening fiber bundles by a spherical deconvolution filtering method, and only retaining the fiber bundles with physiological significance.

Further, the fiber bundle pathway of interest defining module is configured for defining initiate regions of interest, ending regions of interest, passed regions of interest and avoided regions of interest on the standard brain template, and carrying out fiber tracking based on seed points to obtain fiber bundle pathways satisfying the regions of interest.

Further, the fiber bundle pathway of interest defining module is able to use fiber bundle pathways predefined on a fiber bundle atlas.

Further, the fiber bundle pathway projection and segmentation module is configured for nonlinearly registering a defined region of interest of fiber bundles on the standard brain template to a structural image of each subject, and then linearly registering the defined region of interest of fiber bundles to a diffusion image individual space of each subject; and tracking the fibers based on the seed points in an individual space of the subject to obtain the fiber bundle in pathways satisfying the region of interest.

Further, a fiber bundle may be directly linearly registered to an individual space of a subject under the condition that the fiber bundle pathway has been obtained, a fiber bundle of interest is extracted from a fiber tracking result of the whole brain, and the fiber bundle is segmented into a plurality of small segments on average according to a length, each small segment being defined as a node.

Further, the fiber bundle node image index extraction module is configured for performing diffusion tensor imaging (DTI) model fitting on the diffusion magnetic resonance data, calculating anisotropy fraction (FA) and mean diffusivity (MD) values of the whole brain, performing neurite orientation dispersion and density imaging (NODDI) fitting on the diffusion magnetic resonance data, and calculating intracellular volume fraction (ICVF) and orientation dispersion index ODI values of the whole brain; calculating an average value of the above indexes for each node of each fiber bundle.

Further, the machine learning classification and abnormal node locating module is configured for obtaining feature weights of 10 models, respectively, based on a support vector machine (SVM) classifier, with the features of each nerve fiber node as the input and the group label of the subject as the output, using a 10-fold cross validation for a training set of the SVM classifier, and sorting the features from large to small depending on the feature weights. The top 10% features are selected, and node features that appear repeatedly in the top 10% features are counted, so as to determine which nodes on which fiber bundles pathways have the abnormal changes with the different diseases.

The method provided by the present disclosure has the following beneficial effects. The fiber bundle pathways of interest can be obtained from diffusion magnetic resonance data based on the fiber bundle pathway of interest defining module, and the fiber bundle pathways can be finely divided based on the fiber bundle pathway projection and segmentation module. Compared with the related art, the imaging indexes of various diffusion models can be effectively utilized, which have been proved to be closely related to various diseases in previous studies. Further, abnormal fiber bundle segments can be precisely located based on the machine learning classification and abnormal node locating module, so that the white matter-related disease foci can be precisely located. According to the present disclosure, the SVM classifier can estimate the fiber orientation function on each voxel using the constrained spherical deconvolution reconstruction method, to reconstruct the fiber distribution on each voxel, in order to effectively solve the problem of fiber decussating in the related art.

BRIEF DESCRIPTION OF DRAWINGS

In order to more clearly explain the embodiments of the present disclosure or the technical solution in the prior art, the drawings needed in the description of the embodiments or the prior art will be briefly introduced below. Obviously, the drawings in the following description are only some embodiments of the present disclosure, and other drawings can be obtained according to these drawings without creative labor for those skilled in the art.

DESCRIPTION OF EMBODIMENTS

The present disclosure will be further described with reference to the attached drawings. In order to make people in the field better understand the technical solution in this application, the present disclosure will be further explained with the attached drawings. However, this is only part of the embodiments of this application, not all embodiments. Based on the specific embodiments described in this application, other embodiments obtained by other people in the field without creative work shall fall within the scope of the present disclosure.

Figure 1:
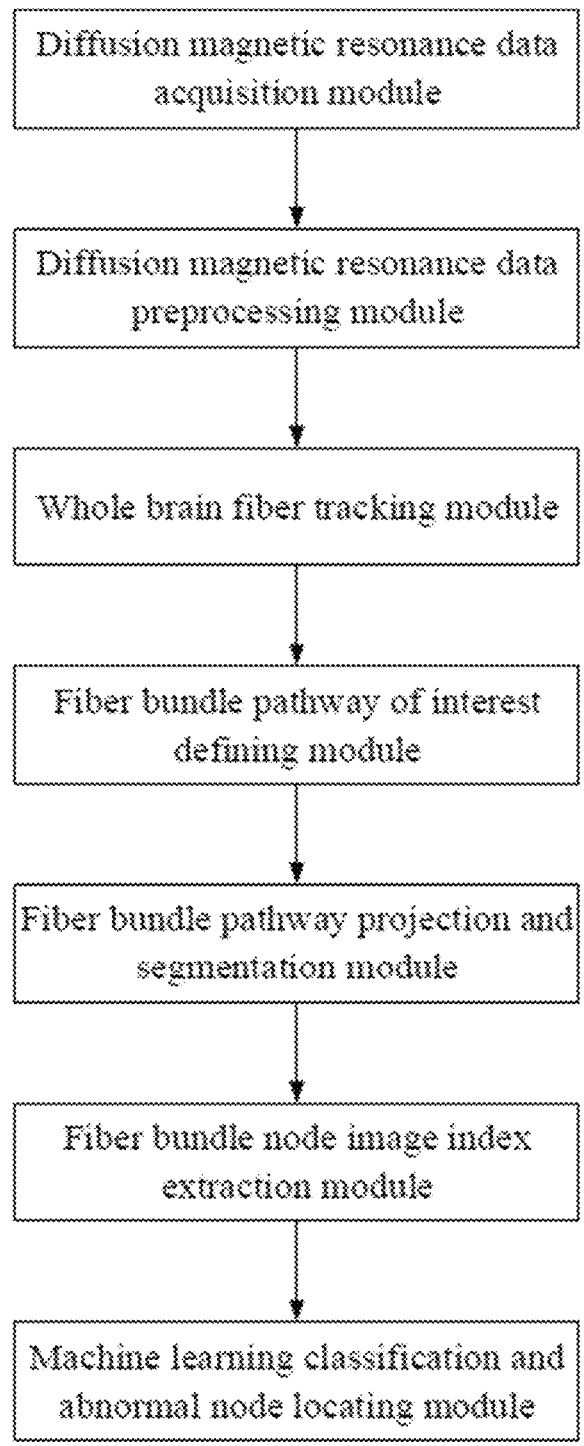
FIG. 1 is a schematic structural diagram of a system for precisely locating abnormal areas of brain fiber bundles provided by the present disclosure.
Figure 2:
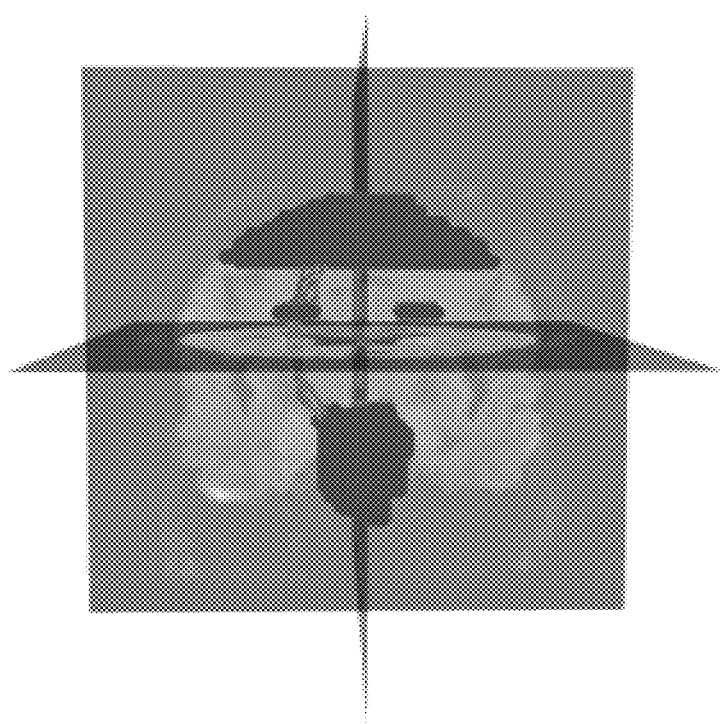
FIG. 2 is a schematic diagram of the fiber bundle pathway construction of the present disclosure.

Generally, the present disclosure provides a system for precisely locating abnormal areas of brain fiber bundles. The system can obtain the fiber bundle pathways of interest, segment them finely, and effectively use the imaging indexes of each diffusion model. Through the method of machine learning, abnormal fiber bundles can be precisely located, and the focus of white matter-related diseases can be precisely located. The schematic diagram of the overall system structure, shown in FIG. 1, includes a diffusion magnetic resonance data acquisition module, a diffusion magnetic resonance data preprocessing module, a whole brain fiber tracking module, a fiber bundle pathway of interest defining module, a fiber bundle pathway projection and segmentation module, a fiber bundle node image index extraction module and a machine learning classification and abnormal node locating module. The diffusion magnetic resonance data acquisition module is configured for acquiring diffusion magnetic resonance data of a disease group and corresponding diffusion magnetic resonance data from a healthy group. The diffusion magnetic resonance data preprocessing module is configured for preprocessing the diffusion magnetic resonance data collected by the diffusion magnetic resonance data acquisition module, and the preprocessing includes image denoising, distortion correction, signal normalization by extracting b0 images, head movement and eddy current correction. The whole brain fiber tracking module is configured for reconstructing a diffusion model of the images based on the data b vector distribution, calculating the response function and the fiber orientation distribution function, and tracking the whole brain fiber. The fiber bundle pathway of interest defining module is configured for defining initiate regions of interest, ending regions of interest, passed regions of interest and avoided regions of interest on the standard brain template MNI152NLinin2009cAsym, and carrying out fiber tracking based on seed points, so as to obtain the fiber bundle pathway satisfying the region of interest. In particular, the fiber bundle pathway predefined on the fiber bundle atlas can further be used, as shown in FIG. 2. The fiber bundle pathway projection and segmentation module is configured for nonlinearly registering the defined fiber bundle region of interest on the standard brain template MNI152NLinin2009cAsym to the structural image of each subject, and then linearly registering to the individual space of the diffusion image of each subject; then, carrying out fiber tracking based on seed points in the individual space of the subject, and obtaining the fiber bundle pathway satisfying the region of interest. Especially, if the fiber bundle pathway has been obtained, the fiber bundle can be directly linearly registered to the individual space of the subject, and then the fiber bundle is segmented into 100 small segments on average according to the length, and each small segment is regarded as a node. The fiber bundle node image index extraction module is configured for obtaining the anisotropy fraction (FA), the mean diffusivity (MD), the intracellular volume fraction (ICVF), the orientation dispersion index (ODI) and the like of each brain region through diffusion magnetic resonance calculation, and calculating the average values of the indexes on the segment of the fiber bundle for each node of each fiber bundle. The machine learning classification and abnormal node locating module is configured for classifying the disease group and the healthy group based on a SVM classifier. The weights of features are obtained by SVM, which can reflect which nodes of which fiber bundles have significant differences between the disease group and the healthy group.

The specific implementation process of the system of the present disclosure is as follows.

The diffusion magnetic resonance data acquisition module is configured for acquiring diffusion magnetic resonance data of a disease group and diffusion magnetic resonance data of a corresponding healthy group. In an example of the present disclosure, the clinical data are collected by the hospital, and the data are divided into type 0 patients, type 1 patients and healthy people according to the clinical manifestations. After data sorting and quality control, 121 patients with type 0, 107 patients with type 1 and 109 healthy people were finally enrolled.

The diffusion magnetic resonance data preprocessing module is configured to denoise and correct the diffusion magnetic resonance data collected by the diffusion magnetic resonance data acquisition module, specifically, the preprocessing of diffusion magnetic resonance image data is completed on the basis of a QSIPrep software package, which specifically includes the following processes: dicom to BIDS format conversion, in which the data are converted into a standard format. Because the signal-to-noise ratio of diffusion magnetic resonance images is low, the principal component analysis (MP-PCA) is configured to denoise the images. Due to the inhomogeneity of B0 field, the diffusion magnetic resonance image will be distorted in the direction of phase gradient, therefore, the image should be subjected to distortion correction (N4 algorithm). The eddy current effect caused by gradient magnetic field switching will produce eddy current that hinders gradient change. This extra disturbance will affect the change of the gradient field, make its waveform seriously distorted, and make the image have geometric deformation, artifacts and other distortions. This effect is called an eddy effect, therefore an eddy correction should be carried out on the data. The breathing and head movement of the subjects during the scanning process may further affect the spatial position of the data, therefore head movement and eddy correction should be carried out on the data.

The whole brain fiber tracking module is configured for extracting the fiber connection of the whole brain based on the preprocessed diffusion magnetic resonance data; specifically, MRtrix3 software is configured to estimate the response function of the preprocessed diffusion magnetic resonance data and reconstruct the fiber orientation distribution model through constrained spherical deconvolution, and because the data contains b vectors of b=0, 1,000 and 2,000, the method of reconstructing the fiber orientation distribution diffusion model by constrained spherical deconvolution is adopted to reconstruct the model; secondly, the whole brain fiber tracking is carried out based on the reconstructed model; the spherical deconvolution model can estimate the dispersion distribution of each voxel; in fiber tracking, a probabilistic fiber tracking method is configured to set seed points in the region of interest, and fiber bundles are tracked from each seed point until the specified number of fiber bundles are completed, which is set to be 10 million fib bundles in the present disclosure; finally, the results of fiber tracking are screened by a spherical deconvolution filtering method of fiber bundles, and the fiber bundles with physiological significance are retained.

The fiber bundle pathway of interest defining module is configured for self-defining the fiber bundle pathway or extract the fiber bundle pathway based on the brain fiber bundle template, further including: defining initiate regions of interest, ending regions of interest, passed regions of interest and avoided regions of interest on the standard brain template on the standard brain template MNI MNI152NLinin2009cAsym, and correcting the regions of interest, such as dividing into the left brain and right brain, etching, removing the extra-cerebral part and the like. Fiber tracking based on seed points is carried out for the selected region of interest, starting from the initial region of interest, passing through or avoiding the corresponding region of interest, reaching the ending region of interest, thereby finally obtaining a fiber bundle pathway satisfying the region of interest. In particular, the corresponding fiber bundle pathway can further be directly extracted from the common fiber bundle template. It should be noted that the fiber bundles of the left and right hemispheres are preferably counted separately. In this example, 80 different fiber bundle pathways were extracted in the present disclosure. Two of the 80 channels were not proposed from any subjects, and the remaining 78 pathways were statistically analyzed (most pathways had more than 100 subjects in each group, and a few pathways had less than 10 subjects in each group).

The fiber bundle pathway projection and segmentation module is configured for projecting the fiber bundle pathway onto the fiber connection result of the whole brain and segmenting, and defining each segment as a node; specifically, based on the features of diffusion magnetic resonance data, the calculation of diffusion magnetic resonance indexes needs to be carried out in the individual space of the subject. Therefore, the present disclosure needs to nonlinearly register the fiber bundle region of interest defined on the standard brain template MNI152NLinin2009cAsym to the structural image of each subject, and then linearly register it to the diffusion image individual space of each subject; then, fiber tracking based on seed points is carried out in the individual space of the subject, and the fiber bundle pathway satisfying the region of interest is obtained. Especially, when the fiber bundle pathway has been obtained, the fiber bundle can be directly linearly registered to the individual space of the subject, and the fiber bundle of interest can be extracted from the fiber tracking results of the whole brain; next, the extracted fiber bundle of interest can be further segmented (e.g., 100 equal parts) by a pyAFQ toolkit by way of an automatic quantitative method, and each segment is regarded as a node.

The fiber bundle node image index extraction module is configured for calculating the fractional anisotropy, mean diffusivity, intra-neurite volume fraction and orientation dispersion index of diffusion magnetic resonance data, so as to obtain the imaging index on each node of each fiber bundle pathway; specifically, the diffusion magnetic resonance data is subjected to diffusion tensor imaging DTI model fitting, and the anisotropy fraction (FA) and the mean diffusivity (MD) of the whole brain are calculated; the diffusion magnetic resonance data is subjected to neurite directional diffusion and density imaging model (NODDI model) fitting, and the intracellular volume fraction (ICVF) and orientation dispersion index (ODI) of the whole brain are calculated. Finally, the average value of the above indexes at each node of each fiber bundle is calculated.

Figure 3:
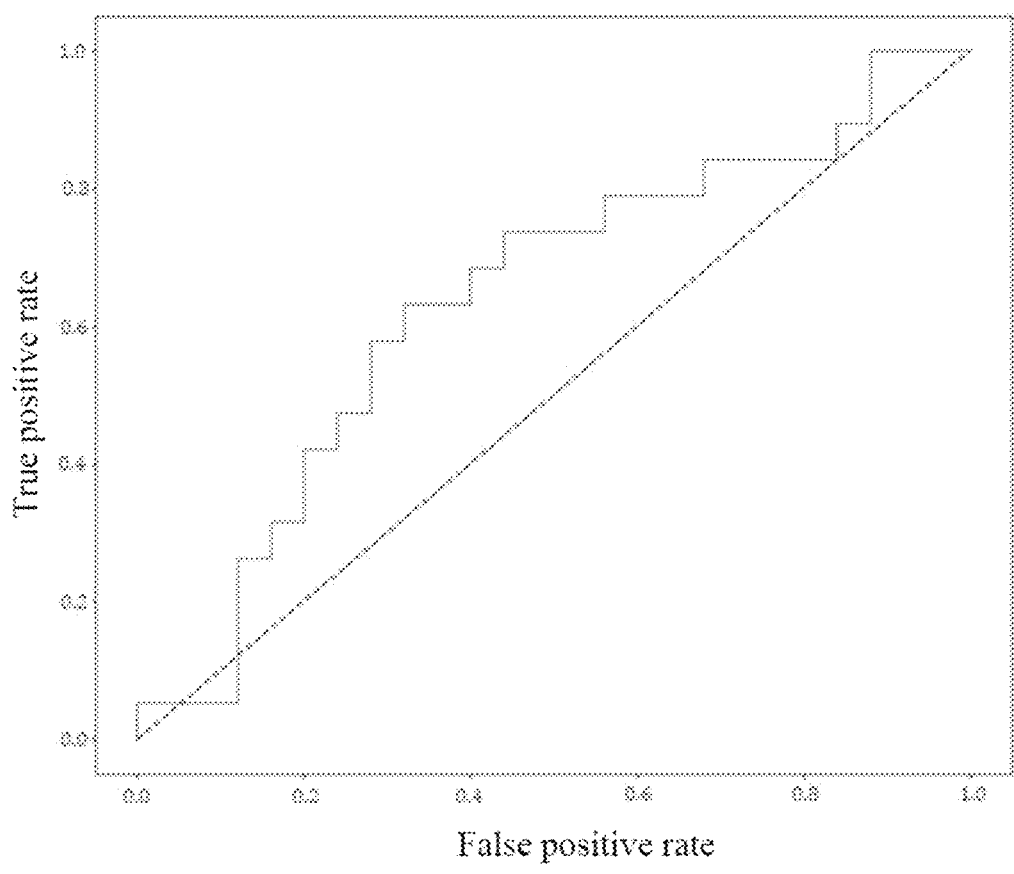
FIG. 3 is a schematic diagram of the AUC value of the classification model test of the present disclosure.

The machine learning classification and abnormal node locating module is configured for classifying the disease group and the healthy group by using imaging indexes through a machine learning method, and locating which nodes on which fiber bundle pathways have abnormal changes with different diseases, further including: counting the fiber bundles jointly tracked for the health group and the disease group, taking 100 node values of these fiber bundles as features, constructing a feature set, taking 0 as the label of the health group and 1 as the label of the disease group, and constructing a label set. The whole data set consists of the feature set and the corresponding label set. Secondly, the data set is randomly divided into a training set and a test set according to a ratio of 8:2. Then, a SVM classifier is configured for binary classification prediction. The kernel function of the SVM classifier is a Linear kernel. The feature of each nerve fiber node is used as the input of the SVM classifier, and the group where the subject is located is used as the label as the output of SVM classifier. The training set uses 10-fold cross validation, and the coef_parameter of the SVM model is configured to obtain all node feature weights in the 10 models after training. The features are sorted from large to small according to the weights, and the features whose weights account for the top 10% of the 10 models are selected, and the node features that appear repeatedly in the top 10% of the features are counted, so as to determine which nodes on which fiber bundle pathways have abnormal changes with different diseases. Finally, a model test is carried out by using the test set to obtain the classification accuracy and AUC value, and the AUC values of the classification model tests of type 0 patients and healthy people are shown in FIG. 3, and the AUC in the embodiment of the present disclosure is 0.64.

In the example of the present disclosure, fiber bundle extraction and segmentation, image index calculation and machine learning abnormal node location were carried out for the clinical data set, and the middle and second half segments of the left and right tractus parietopontinuses were located, and the FA values of the front and back ends of the cortical thalamus pathway were the node features that appear repeatedly in the top 10% features in the classification of type 0 patients and healthy people, as shown in Table 1 below.

TABLE 1

| PPT_L | PPT_R | CT_R |
|---|---|---|
| 1 | 6 | 13 |
| 12 | 7 | 14 |
| 13 | 8 | 15 |
| 14 | 14 | 16 |
| 27 | 15 | 17 |
| 28 | 16 | 18 |
| 29 | 17 | 19 |
| 30 | 45 | 20 |
| 31 | 46 | 21 |
| 37 | 47 | 22 |
| 38 | 48 | 23 |
| 44 | 49 | 24 |
| 45 | 50 | 25 |
| 46 | 51 | 56 |
| 47 | 52 | 57 |
| 48 | 60 | 58 |
| 49 | 61 | 59 |
| 53 | 62 | 91 |
| 54 | 70 | 92 |
| 55 | 71 | 93 |
| 56 | 83 | 94 |
| 71 | 84 | 95 |
| 72 | 88 | 96 |
| 83 | 89 | 97 |
| 89 | 98 | 98 |
| 90 | | |
| 91 | | |
| 92 | | |
| 93 | | |
| 98 | | |

In Table 1, the header is the name of the fiber pathway, and the number is the node position with a great weight during classification. The abnormality of these pathways is closely related to the clinical manifestations of the disease, such as inconvenient movement and rising body fat rate, which shows that the results obtained by this system are well interpretable. Moreover, the system realizes the precise location of abnormal nodes in the fiber bundle pathway, and obtains the fiber bundle segments with inter-group differences between the disease group and the healthy group.

In this application, the term "controller" and/or "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components (e.g., op amp circuit integrator as part of the heat flux data module) that provide the described functionality; or a combination of some or all of the above, such as in a system-on-chip.

The term memory is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

The above-mentioned embodiments are used to explain, rather than to limit the present disclosure. Any modification and change made to the present disclosure within the scope of protection of the spirit and claims of the present disclosure fall within the scope of protection of the present disclosure.

What is claimed is:

1. A system for precisely locating abnormal areas of brain fiber bundles, comprising:
    a diffusion magnetic resonance data acquisition module configured to acquire diffusion magnetic resonance data from a disease group and a healthy group;
    a diffusion magnetic resonance data preprocessing module configured to denoise and correct the diffusion magnetic resonance data acquired by the diffusion magnetic resonance data acquisition module;
    a whole brain fiber tracking module configured to extract fiber connections of a whole brain based on the preprocessed diffusion magnetic resonance data;
    a fiber bundle pathway of interest defining module configured to self-define a fiber bundle pathway or extract a fiber bundle pathway based on a brain fiber bundle template, further comprising: defining initiate regions of interest, ending the regions of interest, passing the regions of interest and avoiding the regions of interest on a standard brain template, and tracking fibers based on seed points to obtain fiber bundle pathways satisfying the regions of interest;
    a fiber bundle pathway projection and segmentation module configured to project the fiber bundle pathway onto a fiber connection result of the whole brain, directly linearly register a fiber bundle to an individual space of a subject when the fiber bundle pathway has been obtained, extract a fiber bundle of interest from a fiber tracking result of the whole brain, and segment the fiber bundle into a plurality of small segments on average according to a length, wherein each small segment is defined as a node;
    a fiber bundle node image index extraction module configured to perform diffusion tensor imaging (DTI) model fitting on the diffusion magnetic resonance data, calculate anisotropy fraction (FA) and mean diffusivity (MD) values of the whole brain, perform neurite orientation dispersion and density imaging (NODDI) fitting on the diffusion magnetic resonance data, and calculate intracellular volume fraction (ICVF) and orientation dispersion index (ODI) values of the whole brain; and calculate an average value of above indexes for each node of each fiber bundle to obtain imaging indexes on each node of each fiber bundle pathway; and
    a machine learning classification and abnormal node locating module configured to classify the disease group and the healthy group by using the imaging indexes through a machine learning method with features of each nerve fiber node as an input of a classifier and a group label of the subject as an output of the classifier, and locate which nodes on which fiber bundle pathways have abnormal changes with different diseases;

wherein the machine learning classification and abnormal node locating module is further configured to obtain feature weights from 10 models generated using a support vector machine (SVM) classifier, respectively, based on the SVM classifier with the features of each nerve fiber node as the input and the group label of the subject belongs as the output, wherein a training set of the SVM classifier uses a 10-fold cross validation, and sort the features from large to small depending on the feature weights, select the top 10% features, and count node features that appear repeatedly in the top 10% features to determine which nodes on which fiber bundles pathways have the abnormal changes with the different diseases.

2. The system for precisely locating abnormal areas of brain fiber bundles according to claim 1, wherein the diffusion magnetic resonance data preprocessing module is further configured to denoise the diffusion magnetic resonance data based on a principal component analysis (PCA) method, correct a distortion based on out-of-phase coded images, and correct head movement and eddy current on the diffusion magnetic resonance data.

3. The system for precisely locating abnormal areas of brain fiber bundles according to claim 1, wherein the whole brain fiber tracking module is further configured to estimate a response function of the preprocessed diffusion magnetic resonance data, reconstruct a fiber orientation distribution diffusion model through constrained spherical deconvolution, and track whole brain fibers based on the reconstructed fiber orientation distribution diffusion model; and screen fiber bundles by a spherical deconvolution filtering method, and retaining the fiber bundles with physiological significance.

4. The system for precisely locating abnormal areas of brain fiber bundles according to claim 1, wherein the fiber bundle pathway of interest defining module is able to use fiber bundle pathways predefined on a fiber bundle atlas.

5. The system for precisely locating abnormal areas of brain fiber bundles according to claim 1, wherein the fiber bundle pathway projection and segmentation module is further configured to nonlinearly register a defined region of interest of fiber bundles on the standard brain template to a structural image of each subject, and then linearly register the defined region of interest of fiber bundles to a diffusion image individual space of each subject; and track the fibers based on the seed points in an individual space of the subject to obtain the fiber bundle pathways satisfying the region of interest.

* * * * *